United States Patent [19]

Wurzburger

[11] Patent Number: 5,528,004
[45] Date of Patent: * Jun. 18, 1996

[54] DISPENSABLE, DISPOSABLE SHIELD FOR STETHOSCOPES

[75] Inventor: Isaac Wurzburger, Monsey, N.Y.

[73] Assignee: M&W Medical Supplies LLC, Monsey, N.Y.

[*] Notice: The term of this patent shall not extend beyond the expiration date of Pat. No. 5,424,495.

[21] Appl. No.: 385,671

[22] Filed: Feb. 8, 1995

Related U.S. Application Data

[63] Continuation of Ser. No. 209,601, Mar. 10, 1994, Pat. No. 5,424,495, which is a continuation-in-part of Ser. No. 106,656, Aug. 16, 1993, abandoned.

[51] Int. Cl.$^6$ .................................................. A61B 7/02
[52] U.S. Cl. .................................................. 181/131
[58] Field of Search .................................. 181/131, 132, 181/137, 171; 128/715, 773, 798, 639; 381/67

[56] References Cited

U.S. PATENT DOCUMENTS

| | | | |
|---|---|---|---|
| 3,867,925 | 2/1975 | Ersek | 181/131 |
| 4,461,368 | 7/1984 | Plourde | 181/131 |
| 4,867,268 | 9/1989 | Ulert | 181/137 |

*Primary Examiner*—Khanh Dang
*Attorney, Agent, or Firm*—Gottlieb Rackman & Reisman

[57] ABSTRACT

A dispensable, disposable shield for stethoscopes prevents the transfer of disease or other contaminants through the incorporation of a disc of plastic film material having a defined edge surface, a pull-tab along the edge surface of the disc, and an adhesive backing on the plastic film material disc, with the plastic film material disc having a contour for covering a diaphragm of the stethoscope and with the adhesive backing covering the entire contour of the disc and being peelably detachable from the stethoscope diaphragm after use. In a second embodiment, the pull-tab is replaced by a flap.

3 Claims, 2 Drawing Sheets

DISPENSABLE, DISPOSABLE SHIELD FOR STETHOSCOPES

This is a continuation of application Ser. No. 08/209,601, filed Mar. 10, 1994, now U.S. Pat. No. 5,424,495 which is a contination-in-part application of application Ser. No. 08/106,656, filed Aug. 16, 1993, now abandoned.

FIELD OF THE INVENTION

This invention relates to medical equipment and accessories, in general, and to a shield for the diaphragm of a stethoscope which serves to provide a barrier to the passage of body-fluids, hair, dirt, skin tissues and any other contaminants from a patient to the stethoscope, in particular.

BACKGROUND OF THE INVENTION

As is well known and understood, stethoscopes are used extensively in medical practice to allow a physician or other provider of medical care to monitor sounds in the respiratory, cardiac, plural, arterial, venus, and other body systems. As is also well known and understood, it is typical for physicians and other care providers to employ this highly used medical instrument from patient to patient, either by constantly having it upon their person, or near at hand, while in the treating environment. (For example, and when carried about, it is not unusual to find the physician or provider of medical care to employ the stethoscope on between 15–20 patients per hour in a hospital environment, and anywhere between 6 and 12 patients in an office setting.) As the acceptable practice, the diaphragm of the stethoscope in such usage is placed directly on the skin of the patients—and, as a result, the entire stethoscope diaphragm thus becomes susceptible to contamination and to the passing of such contamination from patient to patient unless the diaphragm is sterilized between each use. However, as such process is extremely time consuming, a sterilization of the stethoscope diaphragm is not common, even if there existed—which there does not—any recommended procedure for the sterilization of the stethoscope diaphragm.

As is also well appreciated, such danger of contamination being transferred is magnified when used in neo-natal care, where the newborns are most at risk to the transfer of communicable diseases, colds, or other contaminants. Since a stethoscope is often placed at points where such body fluids and contaminants as blood, urine, tears, exist, it becomes even more important that the stethoscope diaphragm either be sterilized between uses, or be shielded in use so as to limit the opportunity for such fluids and contaminants to reach the stethoscope diaphragm itself.

It is also desirable to protect both the patient and the physician from contacting each other near the stethoscope diaphragm in order to prevent the transfer of body fluids and other contaminants between the patient and the physician.

OBJECTS OF THE INVENTION

It is, therefore, an object of the invention to provide a disposable shield for a stethoscope which prevents the passage of body fluids and other contaminants from the patient to the diaphragm of the stethoscope.

It is also an object of the invention to provide a disposable shield for a stethoscope which prevents the passage of body fluids and other contaminants between the patient and the physician.

It is another object of the invention to provide such a disposable shield which can be easily located and identified in a care facility.

It is a further object of the invention to provide such a disposable shield which is easy to apply and remove by the care provider, and in a safe manner.

It is yet another object of the invention to provide such a disposable shield in a dispenser which is simple to manufacturer and utilize, and which can easily be positioned for use at the care facility.

It is another object of the invention to provide such dispensable, disposable shields for stethoscope diaphragms which are exceedingly simple to apply in use, and to discard after use.

BRIEF DESCRIPTION OF THE DRAWING

These and other features of the present invention will be more clearly understood from a consideration of the following description, taken in connection with the accompanying drawings, in which.

DETAILED DESCRIPTION OF THE DRAWINGS

Figure 3:
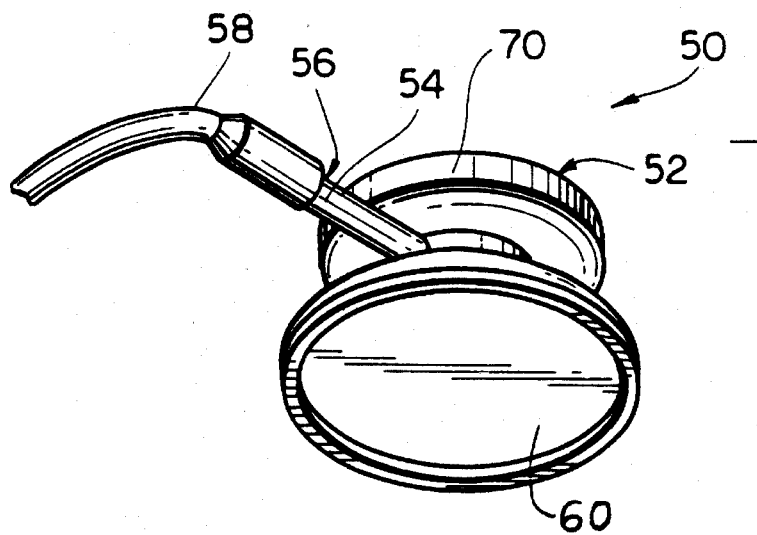
FIG. 3 is an exploded perspective view of a stethoscope having a diaphragm and the shield.
Figure 4:
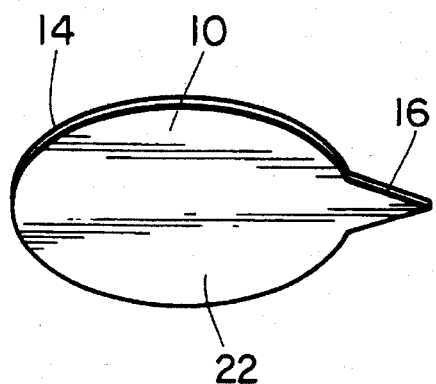
FIG. 4 is a top plan view of the stethoscope of FIG. 3 showing a second embodiment of the disposable shield.
Figure 4:
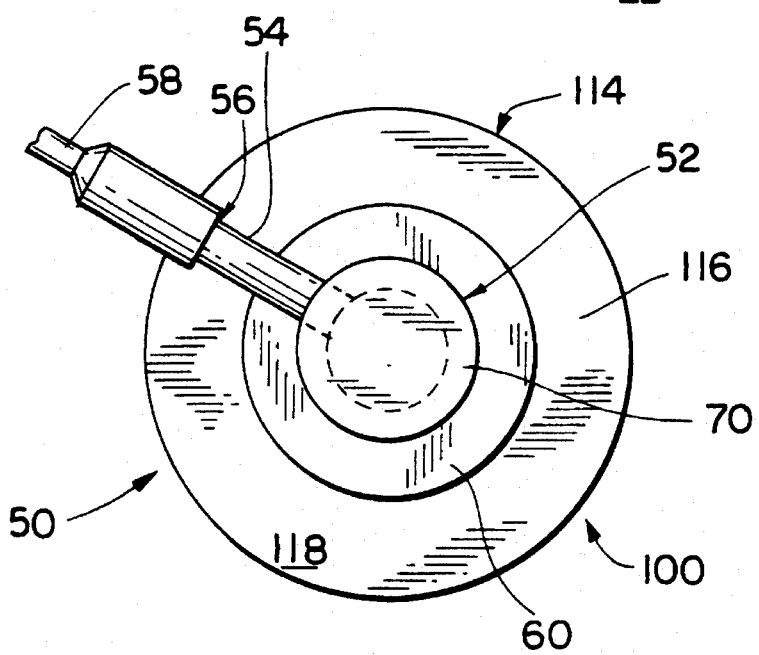

As seen in FIGS. 3 and 4, a stethoscope 50 has a head 52, a diaphragm 60 and a bell chamber 70. A hollow tube 54 extends from head 52 and ends at an end 56. Attached over end 56 of tube 54 is a hose 58, which terminates at two ear plugs (not shown) for placement in the ears of a user of stethoscope 50.

Figure 1A:
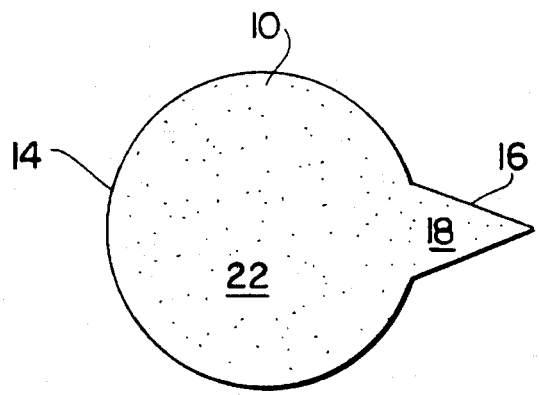
FIGS. 1A and 1B illustrate a preferred embodiment of a disposable shield embodying the principles of the invention.
Figure 1B:
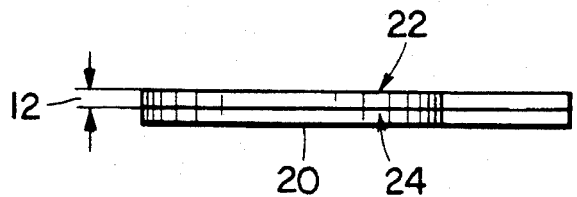

The top view of FIG. 1A and the side view of FIG. 1B are helpful in an understanding that the preferred embodiment of the disposable shield of the invention is composed of a disc 10 of a plastic film material having a predetermined thickness 12 and a defined edge surface 14. A pull-tab 16 extends from the edge surface 14, as at 18, for grasping by the physician or other care provider in temporarily affixing the disc 10 to the diaphragm 60 of stethoscope 50 (see FIGS. 3 and 4), and for detaching and discarding the disc 10 after a single patient use. To such end, the disc 10 has first and second sides 22 and 24, respectively, both sides selected to have a contour to cover diaphragm 60 of stethoscope 50, wherein second side 24 is provided with an adhesive backing 20 if any appropriate composition to secure it to the stethoscope diaphragm 60 so that the entire contour of disc 10 covers the entire surface of diaphragm 60 that touches the patient's body when stethoscope 50 is in use. The use of adhesive backing 20 allows disc 10 to be peelably detachable from diaphragm 60 after patient usage.

Figure 2:
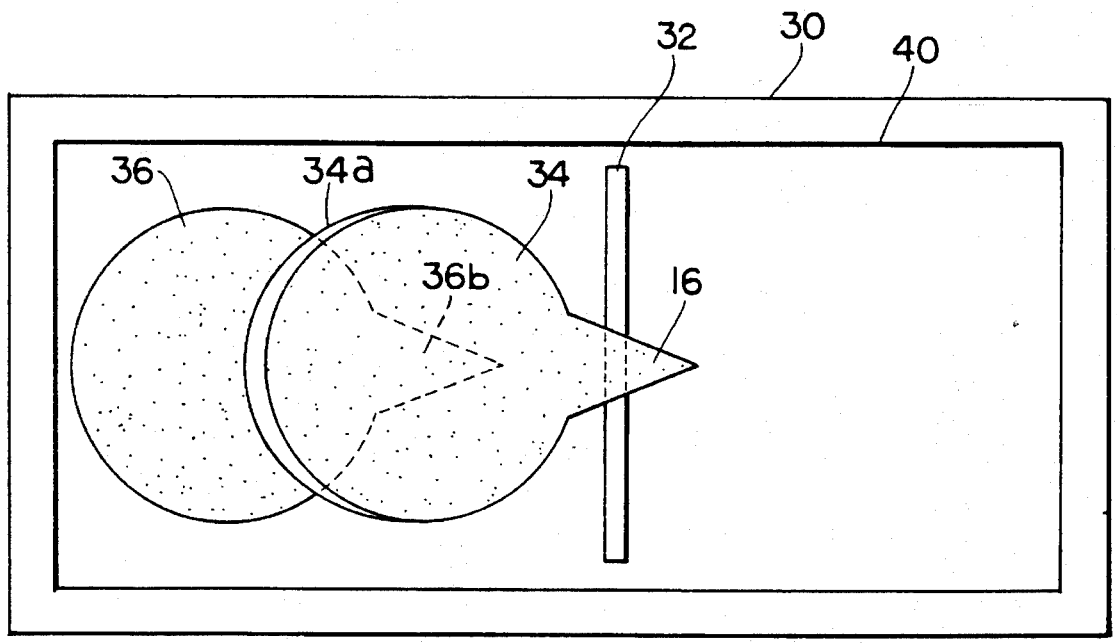
FIG. 2 illustrates a type of dispenser which may be employed with the disposable shield of FIG. 1.

Turning now to FIG. 4, the stethoscope 50 of FIG. 3 is shown with a second embodiment of disc 10, shown at 100. Disc 100 is substantially identical to disc 10 of FIGS. 1–3, except that instead of pull-tab 16, disc 100 has flap 116. Disc 100 has edge 114, which edge defines both the diameter of disc 100 and the circumference of disc 100 and flap 116. Specifically, flap 116 is merely an annular continuation of pull-tab 16 of disc 10. As with pull-tab 16, surface 118 of flap 116 (see FIG. 4) has no adhesive. Flap 116 accordingly achieves two major goals: (1) it is easily graspable by the physician in temporarily affixing disc 100 to diaphragm 60 of stethoscope 50, and for detaching and discarding disc 100 after a single patient use; and (2) it protects against contact between the hand of the physician and the patient's body when stethoscope 50 is used, thereby preventing transfer of body fluids and other contaminants between the patient and the physician. Obviously, and so as not to interfere with the normal use of the stethoscope 50 in allowing the monitoring of sounds in the various body systems, of discs 10 and 100 are selected of a narrow thickness, yet sufficient to sustain use, such as 2 mils thick, in the preferred embodiment of the invention. In accordance with intended usage, the plastic film material may be manufactured to be sterile or non-sterile and packaged as such—and with the peelable adhesive backing 20, could even be affixed to the patient's chart (not shown) after use as an alternative to being discarded—and in such employment, may be fabricated of a matte acetate material, so as to be written upon with pen and ink as part of the patient's treatment history chart.

By further making these shields of a colored, opaque plastic film material, their presence can be most easily noted by the physician and care provider, so that their re-use for the next patient will easily be detected, in assuring that any body fluids, diseases, and/or contaminants will not be transmitted. Such feature fosters the removal of the shield after use, its discarding, and its replacement by a new shield for the next patient to be seen. In utilizing the invention, it will be readily understood that the dimensions selected for the shield and its configuration depends upon intended use—and, typically, a circular configuration of some 1.5 inch diameter for the contour of discs 10 and 100 (i.e., the area over which adhesive backing 20 is applied), will most usually suffice—although, in neo-natal care instances, a smaller diameter for the contour might be employed to fit with the usually smaller stethoscope diaphragm there employed. In any event, the shield will be placed in position on the stethoscope diaphragm 60, and removed from it after use for discarding by the healthcare provider, simply by grasping onto the pull-tab 16 of disc 10 or flap 116 of disc 100—which, as contradistinct from the contour of discs 10 or 100, is devoid of any adhesive backing.

One further feature of the present invention lies in its ready location for use—as, for example, by any appropriate securing to a wall alongside the patient bed in a healthcare facility, or alongside a patient table in an office treatment room. Alternatively, on a counter at either location, a plurality of the discs 10 or 100 may be provided in a dispenser for serial grasping by the medical provider through the existing pull-tab 16, as illustrated by the configuration in FIG. 2, or through flap 116 for discs 100 (not shown). There, a plastic dispenser 30 is shown, with a center slot 32 through which the pull-tab 16 of the first of several discs protrude. As will be appreciated, the adhesive backing 34a of the first disc 34 extends to cover over the pull-tab 36b of the next underlying disc 36 so as to automatically draw the disc 36 into position by pulling on the pull-tab 16 when removing the disc 34 from the dispenser 30 for use. With a disc material thickness of some 2 mils, a dispenser providing up to 50, or even 100, discs can thus be had, in a dispenser having a thickness 40 of approximately 1 inch, or less. Pulling on the tab of an overlying disc in the dispenser 30 thus automatically draws out the tab of the underlying disc immediately adjacent to it. Obviously, the dimensions of the dispenser 30 depend upon the discs to be stored therein, for use with whatever the size and shape of the stethoscope diaphragm might happen to be.

While there has been described what is considered to be preferred embodiments of the present invention, it will be readily appreciated by those skilled in the art that modifications can be made without departing from the scope of the teachings herein. Thus, whereas the preferred embodiments of the invention have been described in employing a plastic film material preferably of matte acetate, any type of composition can be employed—acetate, polyester, or otherwise—as long as the material can be readily affixed to the diaphragm 60 of the stethoscope 50, can be peelably detached therefrom, and of a density and thickness which does not interfere with the monitoring of transmitted sounds from the body systems and cavities. In similar fashion, any type of appropriate adhesive material can be utilized, of a synthetic that affords a sufficient amount of adhesion so as to affix to the stethoscope diaphragm when in use, while being able to be peelably detached for discarding. Additionally, depending upon the diameter of the stethoscope diaphragm, additional manufactures of the dispenser 30 may be employed—even to the extent of replacing the described arrangement of positioning consecutive shields one atop the other with an arrangement wherein the shields are adjacent one another on a continuous roll (not shown), and separated one from another by perforations (not shown) to be cut by serated edges at a slot of a different dispenser through which the plastic film material shields may be drawn. Although possible to strengthen the shield securement to the stethoscope diaphragm by employing types of "elastic bands" around the edges of the disc to exert a holding force on the stethoscope diaphragm when in position, such utilization of these "elastic holding adjuncts" are not as desirable as the arrangement of the described embodiment, and for at least the reason of their added cost and increased bulk in formulating the dispensing package. In either event, it will be appreciated that such use of the plastic film securement also serves to afford a "warmer" touch to the patient's skin than exists with the typically used stethoscope which, by necessity, picks up a cooler temperature from its surrounding room environment just by hanging around the physician's neck or by lying on a counter.

It will thus be seen that the objects set forth above, among those made apparent from the preceding description, are efficiently attained and, since certain changes may be made in the above constructions without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

I claim:

1. For a stethoscope having a diaphragm with a surface for touching the body of a person, and said surface having an area, a shield for said diaphragm of said stethoscope, comprising:

a disc of film material having first and second sides, said first and second sides having a contour comparable to said area of said surface of said diaphragm of said stethoscope; and an adhesive backing on said second side of said disc, wherein said adhesive backing has a contour comparable to the contour of said disc, said adhesive backing for detachably adhering said disc to said surface of said diaphragm of said stethoscope so that said disc entirely covers said surface of said diaphragm of said stethoscope.

2. The shield of claim 1, wherein said disc of plastic film material is of the order of 2 mils thick.

3. The shield of claim 2, wherein said disc of plastic film material is composed of a matte acetate.

* * * * *